United States Patent [19]

Yamada et al.

[11] Patent Number: 5,132,190
[45] Date of Patent: Jul. 21, 1992

[54] HYDROZONES AND ELECTROPHOTOGRAPHIC PHOTORECEPTORS COMPRISING THEM

[75] Inventors: Yasuyuki Yamada, Yokohama; Hiroyuki Akahori, Yokosuka; Katashi Enomoto, Zushi; Hisato Itoh; Tsutomu Nishizawa, both of Yokohama; Akihiro Yamaguchi, Kamakura, all of Japan

[73] Assignee: Mitsui Toatsu Chemicals Incorporated, Tokyo, Japan

[21] Appl. No.: 505,273

[22] Filed: Apr. 9, 1990

[30] Foreign Application Priority Data

| Apr. 10, 1989 | [JP] | Japan | 1-88048 |
| Apr. 28, 1989 | [JP] | Japan | 1-107594 |
| May 25, 1989 | [JP] | Japan | 1-130067 |
| May 25, 1989 | [JP] | Japan | 1-130068 |
| Oct. 9, 1989 | [JP] | Japan | 1-262205 |

[51] Int. Cl.$^5$ .................................. G03G 5/05
[52] U.S. Cl. ............................ 430/59; 430/58; 252/500
[58] Field of Search ............... 430/59, 58; 252/500

[56] References Cited

U.S. PATENT DOCUMENTS

| 4,465,857 | 8/1984 | Neumann et al. | 564/251 |
| 4,477,550 | 10/1984 | Horie et al. | 430/59 |
| 4,728,592 | 3/1988 | Ohaku et al. | 430/59 |
| 4,988,596 | 1/1991 | Ueda | 430/59 |

FOREIGN PATENT DOCUMENTS 3124396 6/1981 Fed. Rep. of Germany.
3208455 3/1982 Fed. Rep. of Germany.

OTHER PUBLICATIONS

Patent Abstracts of Japan, vol. 4, No. 90, Jun. 27, 1980.
Patent Abstracts of Japan, vol. 4, No. 82, Jun. 13, 1980.

*Primary Examiner*—Marion E. McCamish
*Assistant Examiner*—S. Rosasco
*Attorney, Agent, or Firm*—Millen, White & Zelano

[57] ABSTRACT

A hydrazone compound represented by the following formula (I):

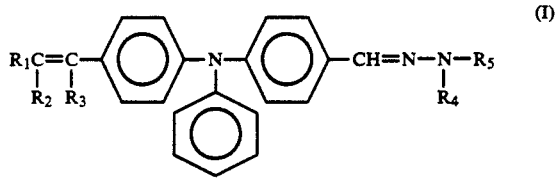

wherein $R_1$ and $R_2$ each are an aryl group or collectively with the carbon to which they are attached form a polycyclic group; $R_3$ represents a hydrogen or halogen atom or an alkyl or phenyl group; and $R_4$ and $R_5$ each represent an alkyl, aralkyl or aryl group, with the proviso that at least one of $R_4$ and $R_5$ is an aryl group, is useful as a charge-transporting material in an electrophotographic photoreceptor and are produced by condensing the corresponding aldehyde with the corresponding $H_2N-NR_4R_5$ hydrazine.

12 Claims, 1 Drawing Sheet

HYDROZONES AND ELECTROPHOTOGRAPHIC PHOTORECEPTORS COMPRISING THEM

BACKGROUND OF THE INVENTION

1. Field of the Invention

The present relates to novel hydrazone compounds, to processes for the preparation thereof and to electrophotographic photoreceptors comprising them, especially to electrophotographic photoreceptors each of which comprise one of the novel hydrazone compounds as a charge-transporting material in a photosensitive layer on an electrically-conductive base.

2. Description of the Prior Art

Inorganic photosensitive materials such as selenium, cadmium sulfide and zinc oxide have heretofore been used widely as photosensitive materials for electrophotographic photoreceptors. Photoreceptors using these photosensitive materials do not, however, fully provide the properties required of electrophotographic photoreceptors, such as sensitivity, light stability, moisture resistance and durability. For example, although photoreceptors based on a selenium material have excellent sensitivity, they have numerous drawbacks, viz., they are prone to crystallize under heat or to deposit smear or the like and their characteristics hence tend to be deteriorated, they are costly as they are fabricated by vacuum deposition, and they cannot satisfactorily be formed into a belt-like configuration due to their lack of flexibility. Photoreceptors using a cadmium sulfide involve problems of moisture resistance and durability, while those employing zinc oxide have a durability problem.

With a view toward overcoming these drawbacks of photoreceptors which use such inorganic photosensitive materials, various photoreceptors using organic photosensitive materials have been investigated.

Among photoreceptors developed to improve such drawbacks, function-separated photoreceptors in which the charge-generating function and the charge-transporting function are assigned to different materials have attracted interest. Since function-separated photoreceptors permit the selection of a material having one of the above two functions and another material having the remaining function or functions from wide ranges of materials and then to use them in combination, it is possible to fabricate photoreceptors having both high sensitivity and high durability.

Electrophotographic characteristics required for a charge-transporting material include:

(1) A sufficiently high ability to receive charges generated by an associated charge-generating material.

(2) An ability to rapidly transport the charges thus received.

(3) An ability to fully transport charges even in a low electric field, so that residual charges do not remain.

In addition, the charge-transporting material is also required to have high durability so that it can remain stable to the light, heat and the like, to which it is repeatedly exposed as a photoreceptor in the course of the repeating steps of charging, exposure, development and transfer upon copying, so that it can thus provide reproduced pictures having high fidelity to the original and good reproduceability.

A variety of compounds have been proposed as charge-transporting materials. For example, poly-N-vinylcarbazole has been known as a photoconducting material for many years. Photoreceptors using this compound as a charge-transporting material have been used commercially. However, this material itself has poor flexibility, is brittle and therefore tends to develop cracks. Accordingly, it has inferior durability with respect to repeated use. When it is used in combination with a binder to improve its flexibility, another problem arises, viz., the electrophotographic characteristics deteriorate.

On the other hand, low molecular weight compounds generally are not film-formers. Therefore, they are generally mixed with a binder at desired ratios to form photosensitive layers. Many charge-transporting materials based on low molecular weight compounds have been proposed. For example, hydrazone compounds have high sensitivity as charge-transporting materials, including those disclosed by way of example in Japanese Patent Laid-Open Nos. 46761/1980, 52064/1980, 58156/1982 and 58157/1982. However, they have a decomposition problem due to the ozone given off upon corona charging or light and heat instability. Although they have excellent initial performance, low-contrast or high fogging pictures are obtained after repeated use because of a reduction in the charge-holding ability or an accumulated residual potential.

Many other charge-transporting materials have also been proposed. However, there is no charge-transporting material which can fully satisfy the performance required as an electrophotographic photoreceptor in actual use. There is hence an outstanding demand for the development of still better photoreceptors.

SUMMARY OF THE INVENTION

An object of the present invention is to provide novel compounds which are useful as a charge-transporting material.

Another object of the present invention is to provide a high-sensitivity and high-durability electrophotographic photoreceptor employing a novel compound of this invention.

These objects of the present invention can be achieved by a novel hydrazone compound represented by the following formula (I):

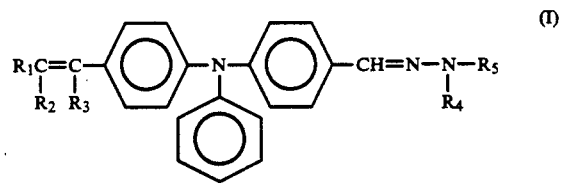

wherein $R_1$ and $R_2$ each represent an aryl group, which can be substituted or unsubstituted, or collectively with the carbon atom to which they are attached a polycyclic group, $R_3$ represents a hydrogen atom, a halogen atom, or phenyl, which may be substituted or unsubstituted, and $R_4$ and $R_5$ individually represent an alkyl, aralkyl or aryl, which aryl groups may be substituted or unsubstituted, with the proviso that at least one of $R_4$ and $R_5$ is an aryl group.

An electrophotographic photoreceptor according to the present invention employs as a charge-transporting material in a photosensitive layer on an electrically-conductive base, a hydrazone compound by the formula (I).

An electrophotographic photoreceptor according to the present invention, which makes use of a hydrazone compound of the present invention, has high sensitivity and exhibits stable performance even when employed repeatedly. Therefore, it also has excellent durability. A photoreceptor of the present invention can be used not only in electrophotographic copy machines but also in various printers and electrophotographic plate-making systems which make use of the principle of electrophotographic copying.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
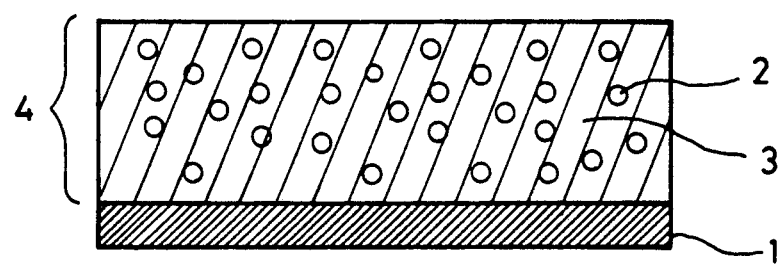
FIGS. 1 and 2 are schematic cross-sectional views illustrating exemplary constructions of an electrophotographic photoreceptor according to the present invention.

Illustrative of the compounds of formula (I) are those wherein
a. one or more of $R_1$, $R_2$, $R_4$ and $R_5$ are phenyl;
b. $R_3$ is a hydrogen or chlorine atom;
c. $R_5$ is methyl or phenyl;
d. each of $R_1$, $R_2$ and $R_4$ is phenyl; and
e. $R_1$ and $R_2$ and the carbon atom to which they are attached are 9-fluorenylidene, 10-xanthenylidene, 10-thioxanthenylidene.

Examples of the aryl group represented by $R_1$ or $R_2$ in the formula (I) are carbocyclic aryl of 6 or more ring carbon atoms and 1-3 rings, e.g., phenyl and naphthyl. The aryl group can bear one, two, three or more substituents, examples of which are alkyl groups, preferably of 1-4 carbon atoms, such as methyl and ethyl, alkoxyl groups, preferably of 1-4 carbon atoms, such as methoxy and ethoxy, halogen atoms such as Cl and Br, and dialkylamino groups, preferably di-lower-alkyl amino groups of 1-4 carbon atoms in each alkyl group, such as dimethylamino and diethylamino. Illustrative examples of the aromatic ring system formed by $R_1$ and $R_2$ collectively with the carbon atom to which $R_1$ and $R_2$ are bonded include 9-fluorenylidene, 10-xanthenylidene and 10-thioxanthenylidene. Examples of the halogen atom represented by $R_3$ include Cl and Br. Illustrative examples of the alkyl group also represented by $R_3$ include methyl, ethyl, and straight or branched chain propyl, butyl and octyl. When $R_3$ is a substituted phenyl group, exemplary substituents include those illustrated for $R_1$ and $R_2$. $R_4$ and $R_5$ may, for example, be methyl, ethyl and straight and branched chain propyl, pentyl, hexyl and octyl as exemplary alkyl groups; benzyl, phenethyl and naphthylmethyl as illustrative aralkyl groups; and phenyl and naphthyl as typical aryl groups. When $R_4$ or $R_5$ is a substituted aryl group, exemplary substituents include those illustrated for $R_1$ and $R_2$. The compound represented by the formula (I) can be prepared by reacting in a suitable solvent a corresponding aldehyde represented by the following formula (II):

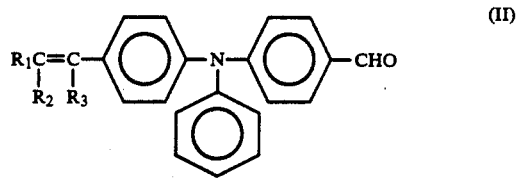

wherein $R_1$, $R_2$ and $R_3$ have the same meanings as defined above for the formula (I), with a hydrazine compound represented by the following formula (III):

wherein $R_4$ and $R_5$ have the same meanings as defined above for the formula (I).

The reaction conditions employed are those conventionally employed in hydrazine-aldehyde condensation reactions.

The hydrazine compound of the formula (III) is ordinarily used in an equimolar amount or somewhat excess molar amount, preferably at a molar ratio of 1.0–1.2 relative to the aldehyde compound of the formula (II). The hydrazine compound may be used in the form of a mineral acid salt such as the hydrochloride.

Exemplary solvents for the reaction are polar solvents, including alcohols such as methanol, ethanol, methylcellosolve and ethylcellosolve, ethers such as tetrahydrofuran and 1,4-dioxane, glycols such as ethylene glycol and propylene glycol, N,N-dimethylformamide, dimethylsulfoxide, and acetic acid. No particular limitation is imposed on the amount of the solvent to be used. The reaction can proceed in either a completely dissolved or suspended state.

The reaction system may be heated to promote the reaction, although the reaction proceeds satisfactorily at room temperature without heating.

An acid can be used to promote the reaction. Exemplary suitable acids include mineral acids, such as hydrochloric acid and sulfuric acid, and organic acids, such as p-toluene sulfonic acid and acetic acid.

The progress of the reaction can be monitored by thin-layer chromatography or high-performance liquid chromatography.

After the completion of the reaction, the intended product can be obtained, for example, by collecting precipitated crystals by filtration or, when no crystals deposit, by diluting the reaction mixture with water or the like and then collecting the resulting precipitate by filtration. The compound of the present invention can then be obtained with high purity by recrystallization, column chromatography or the like.

Aldehydes represented by formula (II) can be obtained in accordance with the so-called Vilsmeier-Haak reaction (A. Vilsmeier, A. Haak; Ber. 60, 119 (1927), in which a triphenylamine represented by formula (II'):

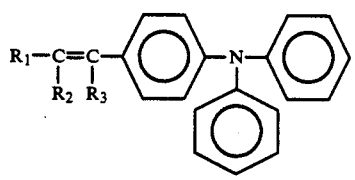

(II')

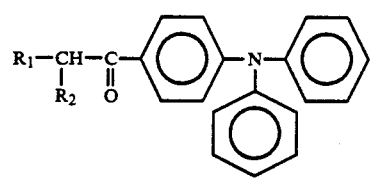

(II")

(Japanese Patent Laid-open No. 198043/1983) is reacted with the Vilsmeier reagent to produce an ammonium salt intermediate, followed by its hydrolysis.

The aldehyde represented by formula (II), in which $R_3$ is a halogen atom (chlorine or bromine), can also be obtained in accordance with the Vilsmeier-Haak reaction, in which halogenation and formylation occur simultaneously, from a triphenylamine represented by formula (II"):

as a raw material.

Examples of the present invention are shown in Table 1. Among the compounds exemplified in Table 1, Exemplary Compound No. 1, No. 2, No. 5, No. 13 and the like are preferred because they have excellent sensitivity and they can be prepared commercially at a low cost.

The compounds represented by the formula (I) in which one or more substituents such as alkyl groups, alkoxyl groups and/or halogen atoms are present on one or more of the benzene rings of the triphenylamine skeletal moiety also exhibit good performance as charge-transporting materials. They are however not advantageous industrially from the standpoint of cost.

TABLE 1

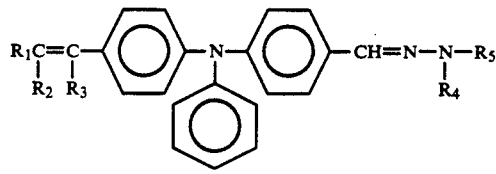

| Exemplary Compound No. | $R_1$ | $R_2$ | $R_3$ | $R_4$ | $R_5$ |
|---|---|---|---|---|---|
| 1 | —Ph | —Ph | H | —Ph | —Ph |
| 2 | —Ph | —Ph | H | —Ph | —CH$_3$ |
| 3 | —Ph | —Ph | H | —Ph | —Naphthyl |
| 4 | —Ph | —Ph | H | —Ph | —C$_6$H$_4$—OCH$_3$ |
| 5 | —Ph | —Ph | —Cl | —Ph | —Ph |
| 6 | —Ph | —Ph | —Cl | —Ph | —C$_6$H$_4$—OCH$_3$ |

TABLE 1-continued $R_1C=C\text{-}C_6H_4\text{-}N(C_6H_5)\text{-}C_6H_4\text{-}CH=N\text{-}N(R_4)R_5$, with $R_2, R_3$ on the carbon bearing $R_1$

| Exemplary Compound No. | R₁ | R₂ | R₃ | R₄ | R₅ |
|---|---|---|---|---|---|
| 7 | –C₆H₄– (phenyl) | –C₆H₄– (phenyl) | –Cl | –C₆H₅ (phenyl) | –CH₃ |
| 8 | –C₆H₄– (phenyl) | –C₆H₄– (phenyl) | –Br | –C₆H₅ (phenyl) | –C₆H₅ (phenyl) |
| 9 | –C₆H₄– (phenyl) | –C₆H₄– (phenyl) | –Br | –C₆H₅ (phenyl) | –CH₃ |
| 10 | –C₆H₄– (phenyl) | –C₆H₄– (phenyl) | –C₆H₄– (phenyl) | –C₆H₅ (phenyl) | –C₆H₅ (phenyl) |
| 11 | –C₆H₄– (phenyl) | –C₆H₄– (phenyl) | –CH₃ | –C₆H₅ (phenyl) | –CH₃ |
| 12 | –C₆H₄– (phenyl) | –naphthyl | H | –C₆H₅ (phenyl) | –CH₃ |
| 13 | fluorenylidene (R₁,R₂ joined) | | H | –C₆H₅ (phenyl) | –C₆H₅ (phenyl) |
| 14 | fluorenylidene (R₁,R₂ joined) | | H | –C₆H₅ (phenyl) | –CH₃ |
| 15 | fluorenylidene (R₁,R₂ joined) | | H | –C₆H₅ (phenyl) | –CH₂–C₆H₅ |
| 16 | dibenzofuran-ylidene (R₁,R₂ joined via O) | | H | –C₆H₅ (phenyl) | –C₆H₅ (phenyl) |

TABLE 1-continued

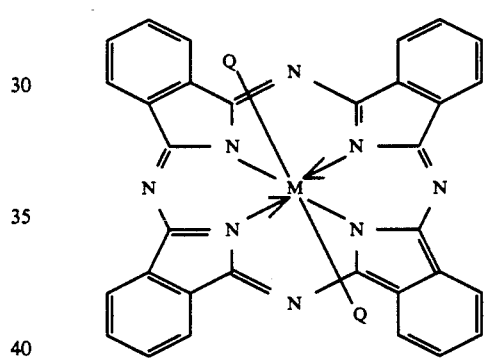

| Exemplary Compound No. | R₁ | R₂ | R₃ | R₄ | R₅ |
|---|---|---|---|---|---|
| 17 | (o-tolyl)-S-(o-tolyl) | | H | naphthyl | —CH₃ |
| 18 | (o-tolyl)-S-(o-tolyl) | | H | phenyl | —CH₃ |

Each of the hydrazone compounds of the present invention can be used as a charge-transporting material in combination with a charge-generating material, whereby an electrophotographic photoreceptor can be constructed.

Any material can be used as the charge-generating material as long as it has charge-generating function. Illustrative of the charge-generating material include inorganic materials such as selenium, selenium alloys, amorphous silicon and cadmium sulfide as well as organic dyes and pigments such as phthalocyanine, perylene, perynone, indigo, anthraquinone, cyanine and azo dyes and pigments. Of these, azo and phthalocyanine charge-generating materials are suitable for use in combination with the charge-transporting materials according to the present invention.

Among these azo and phthalocyanine charge-generating materials, the compounds represented by the following general formulae (IV) and (V), respectively are especially preferred:

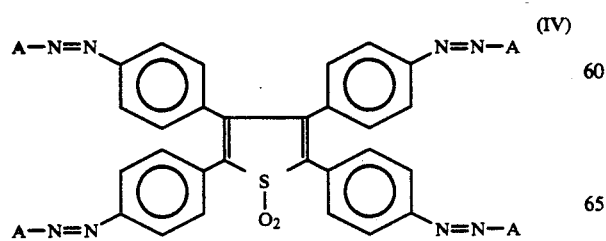

(IV)

wherein each A represents a coupler residuum.

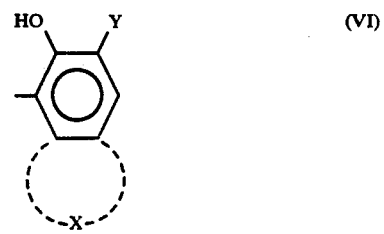

wherein M represents Si, Ge or Sn and Q represents a hydroxyl group or a chlorine, bromine, iodine or fluorine atom.

Various factors may be gathered as reasons for the fact that these combinations are particularly preferred. It is however extremely difficult to fully elucidate such factors under the current technical standard of the present field of art. The combinations of the charge-transporting materials of this invention with the charge-generating materials of the above structural formula (IV) or (V) are based on the surprising finding.

In the formula (IV), illustrative of the coupler residuum represented by A include various groups. For example, there are the following coupler residua (a) and (d):

a) Coupler residua of the following formula (VI):

(VI)

HO, Y on benzene ring fused to X-ring wherein X represents a substituted or unsubstituted cyclic hydrocarbon group or a substituted or unsubstituted heterocyclic ring, and Y represents

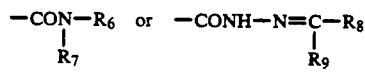

in which $R_6$ represents a substituted or unsubstituted cyclic hydrocarbon group or a substituted or unsubstituted heterocyclic group, $R_7$ a hydrogen atom, a substituted or unsubstituted alkyl group or a substituted or unsubstituted phenyl group, $R_8$ a substituted or unsubstituted cyclic hydrocarbon group, a substituted or unsubstituted heterocyclic group or a substituted or unsubstituted styryl group, and $R_9$ a hydrogen atom, a substituted or unsubstituted alkyl group or a substituted or unsubstituted phenyl group, with the proviso that $R_8$ and $R_9$ may form a ring along with the carbon atoms to which $R_8$ and $R_9$ are bonded, respectively. p X in the formula (VI) is fuxed with the benzene ring to which the hydroxyl group and Y are bonded, and as a result forms a cyclic hydrocarbon ring or heterocyclic ring. Examples of the former include naphthalene and anthracene and examples of the latter include indole, carbazole, benzocarbazole and dibenzofuran rings.

When X has one or more substituents, exemplary substituents include halogen atoms such as Cl and Br and hydroxyl group.

Exemplary cyclic groups represented by $R_6$ and $R_8$ include cyclic hydrocarbon groups such as phenyl, naphthyl, anthryl and pyrenyl and heterocyclic groups such as pyridyl, thienyl, furyl, indolyl, benzofuranyl, carbazolyl and dibenzofuranyl. An example of the ring formed as a result of linking $R_8$ and $R_9$ is a fluorene ring.

When $R_6$ and $R_8$ is a substituted cyclic group, exemplary substituents include alkyl groups such as methyl, ethyl, propyl and butyl, alkoxyl groups such as methoxy, ethoxy, propoxy and butoxy, halogen atoms such as F, Cl and Br, halomethyl groups such as trifluoromethyl, dialkylamino groups such as dimethylamino and diethylamino, nitro group, cyano group, and carboxyl group and esters thereof.

When $R_7$ and $R_9$ is a phenyl group, exemplary substituents thereof include halogen atoms such as Cl and Br.

b) Coupler residua of the following formula (VII) or (VIII):

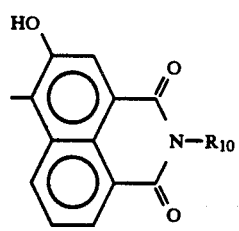 (VII)

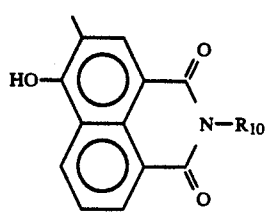 (VIII)

wherein $R_{10}$ represents a substituted or unsubstituted hydrocarbon group.

Illustrative specific groups of $R_{10}$ include alkyl groups such as methyl, ethyl, propyl, butyl and octyl and alkoxyalkyl groups such as methoxyethyl and ethoxyethyl.

c) Coupler residua of the following formula (IX):

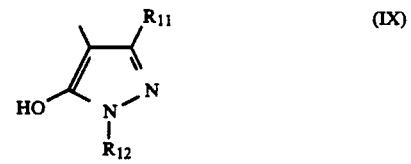 (IX)

wherein $R_{11}$ represents an alkyl group, a carbamoyl group, or a carboxyl group or an ester group thereof, and $R_{12}$ represents a substituted or unsubstituted cyclic hydrocarbon group.

As $R_{12}$, specific examples include cyclic hydrocarbon groups such as phenyl and naphthyl. When these groups are substituted, exemplary substituents include alkyl groups such as methyl, ethyl, propyl and butyl, alkoxyl groups such as methoxy, ethoxy, propoxy and butoxy, dialkylamino groups such as dimethylamino and diethylamino, halogen atoms such as Cl and Br, nitro group, and cyano group.

d) Coupler residua of the following formula (X) or (XI):

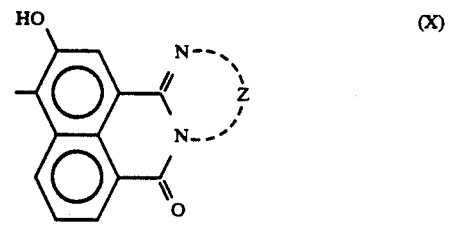 (X)

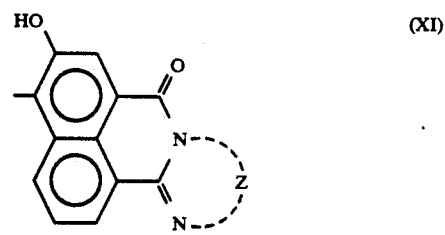 (XI)

wherein Z represents a substituted or unsubstituted divalent cyclic hydrocarbon group or a substituted or unsubstituted divalent heterocyclic group.

As Z, specific examples include divalent monocyclic aromatic hydrocarbon groups such as o-phenylene, divalent fused polycyclic aromatic hydrocarbons such as o-naphthylene, peri-naphthylene, 1,2-anthraquinonylene and 9,10-phenanthrylene, and divalent heterocyclic groups such as pyrazol-3,4-diyl, pyridin-2,3-diyl, pyrimidin-4,5-diyl, imidazol-6,7-diyl, benzimidazol-5,6-diyl and quinolin-6,7-diyl. When these cyclic groups are substituted, exemplary substituents include alkyl groups such as methyl, ethyl, propyl and butyl, alkoxyl groups such as methoxy, ethoxy, propoxy and butoxy, dialkylamino groups such as dimethylamino and diethylamino, halogen atoms such as Cl and Br, nitro group, and cyano group.

Among the coupler residua exemplified above, those represented by the formula (VI) are most preferred because they have high light sensitivity, their intermediate materials are readily available, and they can be prepared at a low cost.

Particularly preferred are those represented by the formula (VI) in which X is fused with the benzene ring, to which the hydroxyl group and Y are bonded, to form a naphthalene ring.

Described more specifically, tetrakisazo compounds useful in the practice of the present invention include those represented by the following structural formulae A-1 through A-155, respectively, which correspond to the coupler residuum of the formula (IV).

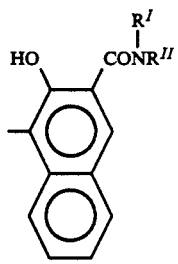

| Compound | $R^{II}$ | $R^{I}$ |
|---|---|---|
| A-1 | phenyl | H |
| A-2 | 2-methylphenyl | H |
| A-3 | 4-methylphenyl | H |
| A-4 | 2,4-dimethylphenyl | H |
| A-5 | 4-methoxyphenyl | H |
| A-6 | 4-ethylphenyl | H |
| A-7 | 2-ethoxyphenyl | H |
| A-8 | 4-chlorophenyl | H |
| A-9 | 2-chlorophenyl | H |
| A-10 | 4-(n-butyl)-phenyl | H |
| A-11 | 3-bromophenyl | H |
| A-12 | 4-bromophenyl | H |
| A-13 | 2-bromophenyl | H |
| A-14 | 4-trifluoromethyl-phenyl | H |
| A-15 | 2-trifluoromethyl-phenyl | H |
| A-16 | 3-trifluoromethyl-phenyl | H |
| A-17 | 4-cyanophenyl | H |
| A-18 | 3-cyanophenyl | H |
| A-19 | 2-cyanophenyl | H |
| A-20 | 4-nitrophenyl | H |
| A-21 | 3-nitrophenyl | H |
| A-22 | 2-nitrophenyl | H |
| A-23 | 2,4-dimethoxyphenyl | H |
| A-24 | 2,5-dimethylphenyl | H |
| A-25 | 2,5-dimethoxyphenyl | H |
| A-26 | 2,5-diethoxyphenyl | H |
| A-27 | 4-ethoxycarbonyl-phenyl | H |
| A-28 | 2-methyl-5-chlorophenyl | H |
| A-29 | 4-diethylaminophenyl | H |
| A-30 | 4-dimethylaminophenyl | H |
| A-31 | 2-methyl-4-chlorophenyl | H |
| A-32 | 2-methyl-4-methoxyphenyl | H |
| A-33 | 2-nitro-4-methoxyphenyl | H |
| A-34 | 2-methoxy-5-bromophenyl | H |
| A-35 | 4-carboxy-phenyl | H |
| A-36 | 4-n-propoxy-phenyl | H |
| A-37 | 4-n-butoxy-phenyl | H |
| A-38 | 4-t-butoxy-phenyl | H |
| A-39 | 2,5-dimethoxy-4-chlorophenyl | H |
| A-40 | α-naphthyl | H |
| A-41 | β-naphthyl | H |
| A-102 | 3-dibenzofuranyl | H |
| A-103 | 3-carbazoly | H |
| A-104 | phenyl | $CH_3$ |
| A-105 | p-tolyl | $CH_3$ |
| A-106 | 2,5-dimethoxyphenyl | $CH_3$ |
| A-107 | phenyl | phenyl |

-continued

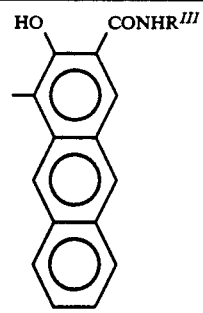

| Compound | $R^{III}$ |
|---|---|
| A-42 | p-tolyl |
| A-43 | 2,4-dimethyl-phenyl |
| A-44 | 2-methoxy-phenyl |

| Compound | $R^{IV}$ |
|---|---|
| A-45 | o-tolyl |
| A-46 | m-tolyl |
| A-47 | p-tolyl |
| A-48 | 2,4-dimethylphenyl |
| A-49 | 4-methoxyphenyl |
| A-50 | 4-ethylphenyl |
| A-51 | 2-ethoxyphenyl |
| A-52 | 4-chlorophenyl |
| A-53 | 2-chlorophenyl |
| A-54 | 4-n-propylphenyl |
| A-55 | 3-bromophenyl |
| A-56 | 4-bromophenyl |
| A-57 | 2-bromophenyl |
| A-58 | 4-trifluoromethylphenyl |
| A-59 | 2-trifluoromethylphenyl |
| A-60 | 3-trifluoromethylphenyl |
| A-61 | 4-cyanophenyl |
| A-62 | 3-cyanophenyl |
| A-63 | 2-cyanophenyl |
| A-64 | 4-nitrophenyl |
| A-65 | 3-nitrophenyl |
| A-66 | 2-nitrophenyl |
| A-67 | 2,4-dimethoxyphenyl |
| A-68 | 2,4-dimethylphenyl |
| A-69 | 2,5-dimethoxyphenyl |
| A-70 | 2,4-diethoxyphenyl |
| A-71 | 4-carboxyphenyl |
| A-72 | 2-methyl-5-chlorophenyl |
| A-73 | 4-dimethylaminophenyl |
| A-74 | 4-diethylaminophenyl |
| A-75 | 2-methyl-4-chlorophenyl |
| A-76 | 2-methyl-4-methoxyphenyl |
| A-77 | 2-nitro-4-methoxyphenyl |
| A-78 | 2-methoxy-5-bromophenyl |
| A-79 | 4-n-propoxy-phenyl |
| A-80 | 4-n-butoxyphenyl |
| A-152 | 3-chlorophenyl |
| A-153 | 2-nitro-4-chlorophenyl |
| A-154 | α-naphthyl |
| A-155 | 2-nitro-4-trifluoromethyl-phenyl |

-continued

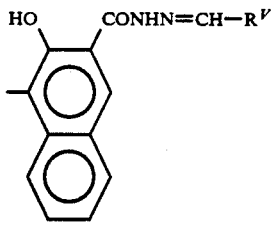

| Compound | $R^V$ |
|---|---|
| A-81 | p-tolyl |
| A-82 | o-tolyl |
| A-83 | m-tolyl |
| A-84 | 4-methoxyphenyl |
| A-85 | 4-dimethylamino-phenyl |
| A-86 | 4-nitrophenyl |
| A-87 | 2-nitrophenyl |
| A-88 | 3-nitrophenyl |
| A-89 | 4-chlorophenyl |
| A-90 | 2-chlorophenyl |
| A-91 | 3-chlorophenyl |
| A-108 | -anthracenyl |
| A-109 | 2-(N-ethyl)carbazolyl |
| A-110 | 2-thienyl |

| Compound | $R^{VI}$ |
|---|---|
| A-92 | phenyl |
| A-93 | p-tolyl |
| A-94 | m-tolyl |
| A-95 | o-tolyl |
| A-96 | 4-nitrophenyl |
| A-97 | 2-nitrophenyl |
| A-98 | 3-nitrophenyl |
| A-99 | 4-dimethylaminophenyl |
| A-100 | 4-cyano-phenyl |
| A-101 | 4-chloro-phenyl |
| A-102 | |
| A-103 | |

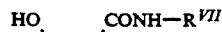

| Compound | $R^{VII}$ |
|---|---|
| A-111 | phenyl |
| A-112 | 4-methoxy-phenyl |
| A-113 | 2,4-dimethyl-phenyl |

-continued

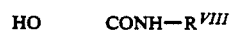

| Compound | $R^{VIII}$ |
|---|---|
| A-114 | 2,5-dimethoxy-phenyl |
| A-115 | p-chlorophenyl |
| A-116 | p-nitrophenyl |

| Compound | $R^{IX}$ |
|---|---|
| A-117 | —CH$_3$ |
| A-118 | —C$_2$H$_5$ |
| A-119 | C$_2$H$_4$OCH |
| A-120 | C$_4$H$_9$(n) |
| A-121 | —C$_2$H$_4$OC$_2$H$_5$ |

| Compound | $R^X$ |
|---|---|
| A-122 | —CH$_3$ |
| A-123 | —C$_3$H$_7$(n) |
| A-124 | —C$_2$H$_4$OCH$_3$ |
| A-125 | —C$_2$H$_5$ |

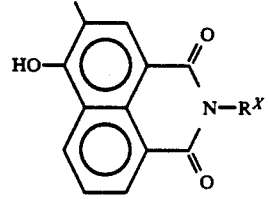

| Compound | $R^{XI}$ | $R^{XII}$ |
|---|---|---|
| A-126 | phenyl | |
| A-127 | p-tolyl | |
| A-128 | 4-chlorophenyl | |
| A-129 | 4-dimethylamino-phenyl | |
| A-130 | 4-cyano-phenyl | |
| A-131 | phenyl | —COOCH$_3$ |
| A-132 | phenyl | —COOH |
| A-133 | 2,4-dinitrophenyl | —CH$_3$ |

-continued

| Compound | $R^{XIII}$ |
|---|---|
| A-134 | H |
| A-136 | 4-methyl |
| A-138 | 5-methyl |
| A-140 | 4,5-dimethyl |
| A-142 | 4,5-benzo |
| A-144 | 4-nitro |
| A-146 | 4-chloro |
| A-150 | 4-dimethylamino |

| Compound | $R^{XIV}$ |
|---|---|
| A-135 | H |
| A-137 | 4-methyl |
| A-139 | 5-methyl |
| A-141 | 4,5-dimethyl |
| A-143 | 4,5-benzo |
| A-145 | 4-nitro |
| A-147 | 4-chloro |
| A-151 | 4-dimethylamino |

A-148

A-149

Specific examples of the phthalocyanine compound represented by the formula (V) are shown in Table 2.

TABLE 2

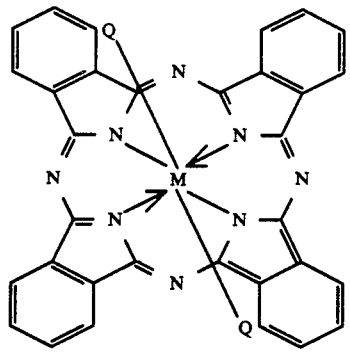

| Exemplary Compound No. | M | Q |
|---|---|---|
| P-1 | Si | OH |
| P-2 | Si | Cl |
| P-3 | Si | Br |
| P-4 | Si | F |
| P-5 | Si | I |
| P-6 | Sn | OH |
| P-7 | Sn | Cl |
| P-8 | Sn | Br |
| P-9 | Sn | F |
| P-10 | Sn | I |
| P-11 | Ge | OH |
| P-12 | Ge | Cl |
| P-13 | Ge | Br |
| P-14 | Ge | I |

The hydrazone compounds according to the present invention do not have film-forming capability by themselves. They therefore are used in combination with a binder to form photosensitive layers. An electrically-insulating high molecular polymer is used as the binder. Illustrative examples of the binder include polystyrene, polyacrylamide, polyvinyl chloride, polyester resins, polycarbonate resins, epoxy resins, phenoxy resins, and polyamide resins.

In particular, polyester resins and polycarbonate resins can suitably be used. A poly-N-vinylcarbazole which per se has charge-transporting ability can also be used as a binder.

Figure 2:
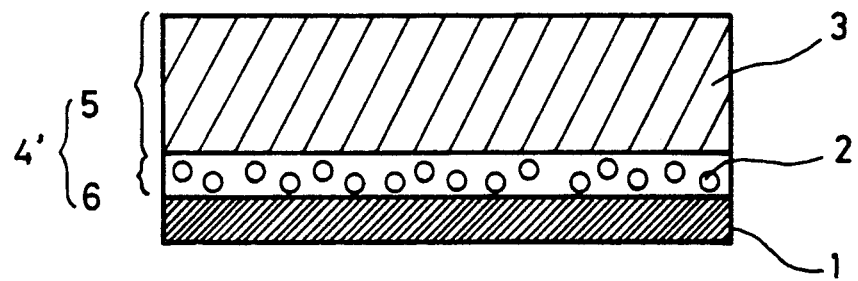

Typical constructions of the photoreceptor are illustrated in FIG. 1 and FIG. 2, respectively. The photoreceptor shown in FIG. 1 is constructed of an electrically-conductive base 1 and a dispersion-type photosensitive layer 4 provided on the base 1. In the photosensitive layer 4, a charge-generating material 2 and a charge-transporting material 3 are dispersed in a binder. The photoreceptor depicted in FIG. 2 is constructed of an electrically-conductive base 1 and a layer-built photosensitive layer 4' provided on the base 1. The photosensitive layer 4' is formed of a charge-generating layer 6 with a charge-generating material 2 dispersed in a binder and a charge-transporting layer 5 with a charge-transporting material 3 dispersed in a binder. As a modification of the photoreceptor of FIG. 2, the charge-generating layer and charge-transporting layer can be reversed in position. The photoreceptors of the above constructions are all effective for the present invention. The layer-built photoreceptor shown in FIG. 2 is preferred in that excellent electrophotographic characteristics are available.

For the fabrication of the photoreceptor, any one of conventionally known methods can be used. In the case of a layer-built photoreceptor for example, fine particles of a charge-generating material are dispersed in a solution in which a binder is dissolved, the resultant dispersion is coated on an electrically-conductive base, and the thus-coated base is then dried to obtain a charge-generating layer. A solution in which a charge-transporting material and a binder are dissolved is then coated over the charge-generating layer and dried, whereby a charge-transporting layer is formed. Other processes can be used for the formation of the charge-generating layer, including, for example, vacuum deposition of the charge-generating material, and coating of a solution of the charge-generating material and subsequent drying. The charge-generating layer can therefore be formed from the charge-generating material by choosing a desired method. The coating is conducted by a usual method, for example, by means of a doctor blade or wire bar or by the dipping method. The optimum thickness range of the photosensitive layer varies depending on the type of the photoreceptor. For example, in the case of photoreceptors as shown in FIG. 1, the thickness range is preferably 3–50 μm, more preferably 5–30 μm.

Further, in the case of photoreceptors as illustrated in FIG. 2, the thickness of the charge-generating layer 6 is preferably 0.01–5 μm, more preferably 0.05–2 μm. Thicknesses smaller than 0.01 μm are too thin to generate sufficient charges. Thicknesses greater than 5 μm result in a high residual potential and are not preferred from the practical viewpoint. On the other hand, the thickness of the charge-transporting layer is preferably 3–50 μm, with 5–30 μm being more preferred. If this thickness is smaller than 3 μm, it is difficult to hold a sufficient quantity of electrical energy. Thicknesses greater than 50 μm result in a high residual potential and are hence not preferred from the practical viewpoint. One or more charge-transporting materials other than the hydrazone compounds of the present invention can also be used in combination with one or more of the hydrazone compounds of the present invention by incorporating the former charge-transporting materials along with the latter charge-transporting materials into the charge-transporting layer. The charge-transporting layer contains one or more charge-transporting materials, at least one of which is a hydrazone compound of the present invention, in a total proportion of 10–95 wt. %, preferably 30–90 wt. %. No substantial transportation of charges takes place if the proportion of the charge-transporting material is smaller than 10 wt.%. Proportions greater than 95 wt.% however result in photoreceptors having poor mechanical strength. It is therefore not preferred from the practical viewpoint to incorporate the charge-transporting material in any proportions outside the above range.

An intermediate layer may be provided between the photosensitive layer and the electrically-conductive base. As the material of the intermediate layer, polyamide, nitrocellulose, casein, polyvinyl alcohol or the like is preferred. The thickness of the intermediate layer is preferably not greater than 1 μm.

As has been described above, electrophotographic photoreceptors according to the present invention can each fabricated by incorporating, in addition to one of the hydrazone compounds of the present invention, the above-described electrically-conductive base, charge-generating material, binder, etc. No particular limitation is imposed on other elements of the photoreceptors as long as they can serve as elements for the photoreceptors.

The present invention will hereinafter be described specifically by the following examples. It should however be borne in mind that the invention is not limited by or to them.

EXAMPLE 1

Synthesis of Exemplary Compound No. 1

An aldehyde compound (2.7 g) represented by the following structural formula:

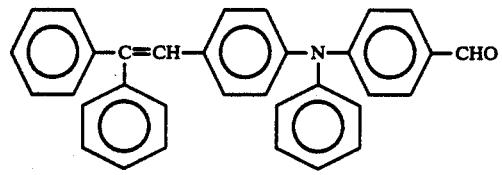

and 1.5 g of 1,1-diphenylhydrazine hydrochloride were mixed with and dissolved in 50 ml of N,N-dimethylformamide. The resultant mixture was stirred for 3 hours at room temperature. After the starting aldehyde compound had been confirmed to be used up, 50 ml of water were added, and the resulting precipitate was collected by filtration and then dried. The crude product was dissolved in a small amount of ethyl acetate, followed by the addition of ethanol. The resulting precipitate was collected by filtration and then dried, whereby 3.0 g of yellow powder (sintered at 92° C. and higher) were obtained. From elemental analysis data and an infrared absorption spectrum, it was confirmed to be Exemplary Compound No. 1.

Its purity was found to be 99.9% by high-performance liquid chromatography.

| Elemental analysis data: | C | H | N |
|---|---|---|---|
| Calculated (%) | 87.52 | 5.67 | 6.81 |
| Found (%) | 87.68 | 5.54 | 6.77 |

EXAMPLE 2

Synthesis of Exemplary Compound No. 2

The aldehyde compound (4.5 g) represented by the following structural formula:

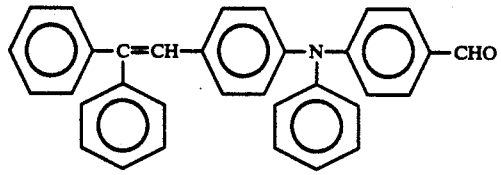

was dissolved in 80 ml of N,N-dimethylformamide. After 1.3 g of 1-methyl-1-phenylhydrazine were added, 0.5 ml of 1N hydrochloric acid was added. The resultant mixture was stirred for 4 hours at room temperature. After the starting aldehyde compound had been confirmed to be used up, 300 ml of water were added gradually, and the resulting precipitate was collected by filtration and then dried. The crude product was recrystallized from ethyl acetate-methanol, whereby 5.4 g of yellow powder (sintered at 84.5° C. and higher) were obtained. From elemental analysis data and an infrared absorption spectrum, it was confirmed to be Exemplary Compound No. 2. Its purity was found to be 99.9% by high-performance liquid chromatography.

| Elemental analysis data: | C | H | N |
| --- | --- | --- | --- |
| Calculated (%) | 86.49 | 5.94 | 7.57 |
| Found (%) | 86.34 | 5.95 | 7.53 |

| Elemental analysis data: | C | H | N | Cl |
| --- | --- | --- | --- | --- |
| Calculated (%) | 87.89 | 5.22 | 6.45 | 5.45 |
| Found (%) | 82.54 | 5.03 | 6.32 | 5.62 |

REFERENTIAL EXAMPLE 1

The aldehyde compound used in Examples 1 and 2 was synthesized in the following manner.

In 200 ml of N,N-dimethylformamide were dispersed 28.7 g of a triphenylamine compound represented by the following formula:

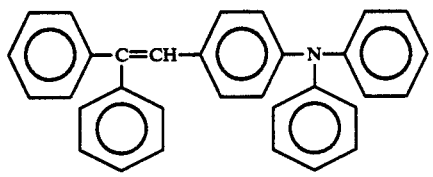

At 0°–5° C., 15.6 g of phosphorus oxychloride were added dropwise. After the resultant mixture was stirred for 1 hour at the same temperature, it was heated to 70°–75° C. and then stirred for 3 hours. The reaction mixture was cooled to room temperature and then poured into 800 ml of ice water. An aqueous solution of sodium hydroxide was added to the resultant mixture to alkalify the latter. The mixture thus obtained was stirred for 1 hour at room temperature, and the resulting precipitate was collected by filtration and then dried. It was recrystallized from water-containing ethanol, whereby 20.5 g of yellow crystals (sintered at 65° C. and higher) were obtained.

EXAMPLE 3

Synthesis of Exemplary Compound No. 5

An aldehyde compound (4.7 g) represented by the following structural formula:

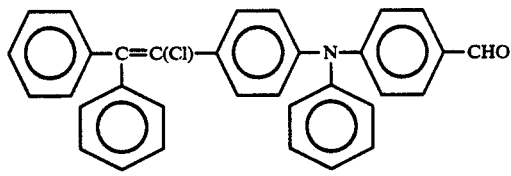

and 2.4 g of 1,1-diphenylhydrazine hydrochloride were mixed with and dissolved in 100 ml of N,N-dimethylformamide. The resultant mixture was stirred for 5 hours at room temperature. Water (150 ml) was added to the reaction mixture, and the resulting precipitate was collected by filtration, washed with water, washed with methanol and then dried.

The crude product was recrystallized from chloroformethanol, whereby 5.7 g of pale yellow crystals (m.p. 191°–192.5° C.) were obtained. From elemental analysis data and an infrared absorption spectrum, it was confirmed to be Exemplary Compound No. 5.

Its purity was found to be 99.8% by high-performance liquid chromatography.

REFERENTIAL EXAMPLE 2

The aldehyde compound used in Example 3 was synthesized in the following manner.

In 100 ml of N,N-dimethylformamide were dissolved 43.9 g of a triphenylamine compound represented by the following formula:

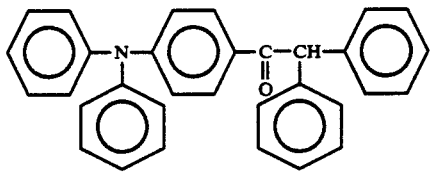

At 0° C., 23 g of phosphorus oxychloride were added dropwise. After the resultant mixture was stirred at 0° C. for 1 hour, it was heated to 80° C over 2 hours and then stirred for 4 hours at 80°–85° C. The reaction mixture was poured into 1 l of ice water. An aqueous solution of sodium hydroxide was added to the resultant mixture to alkalify the latter. The resulting precipitate was collected by filtration, washed with water and then dried, whereby a crude aldehyde compound was obtained. The crude aldehyde compound was purified by chromatography on a silica gel column (eluent: benzene), so that 19 g of pale yellow crystals (m.p. 146.7°–148.3° C.) were obtained.

EXAMPLE 4

Synthesis of Exemplary Compound No. 13

An aldehyde compound (5.2 g) represented by the following structural formula:

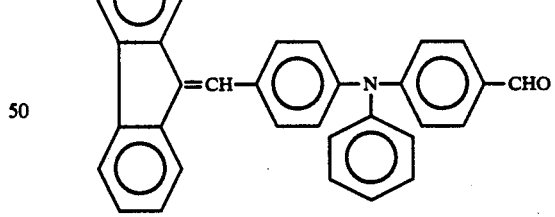

and 2 8 g of 1,1-diphenylhydrochloride were mixed with and dissolved in 100 ml of N,N-dimethylformamide. The resultant mixture was stirred for 5 hours at room temperature. After the starting aldehyde compound had been confirmed to be used up, 300 ml of water were added, and the resulting precipitate was collected by filtration and then dried. It was recrystallized from chloroform-ethanol, whereby 5.9 g of yellow crystals (m.p. 163°–165.5° C.) were obtained. From elemental analysis data and an infrared absorption spectrum, it was confirmed to be Exemplary Compound No. 13. Its purity was found to be 99.8% by high-performance liquid chromatography.

| Elemental analysis data: | C | H | N |
|---|---|---|---|
| Calculated (%) | 87.81 | 5.37 | 6.83 |
| Found (%) | 87.84 | 5.31 | 6.71 |

EXAMPLE 5

Synthesis of Exemplary Compound No. 14

The aldehyde compound (4.0 g) represented by the following structural formula:

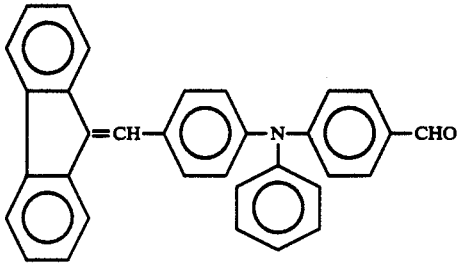

was dissolved in 50 ml of N,N-dimethylformamide. After 1.1 g of 1-methyl-1-phenylhydrazine were added, 0.5 ml of 1N hydrochloric acid was added. The resultant mixture was stirred for 3 hours at room temperature. After the starting 0 aldehyde compound had been confirmed to be used up, 200 ml of water were added. The resulting precipitate was collected by filtration, dried and then recrystallized from chloroform-methanol, whereby 4.9 g of yellow crystals (m.p. 198°-199.5° C.) were obtained. From elemental analysis data and an infrared absorption spectrum, it was confirmed to be Exemplary Compound No. 14. Its purity was found to be 99.9% by high-performance liquid chromatography.

| Elemental analysis data: | C | H | N |
|---|---|---|---|
| Calculated (%) | 86.80 | 5.61 | 7.59 |
| Found (%) | 86.71 | 5.54 | 7.53 |

REFERENTIAL EXAMPLE 3

The aldehyde compound used in Examples 4 and 5 was synthesized in the following manner.

In 30 ml of N,N-dimethylformamide were dispersed 4.4 g of a lriphenylamine compound m.p. 45°-151.5° C.) represented by the following formula:

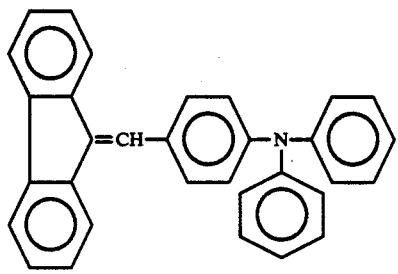

At 0°-5° C., 3.2 g of phosphorus oxychloride were added dropwise. After the resultant mixture was stirred for 1 hour at 10 the same temperature, it was heated to 70°-75° C. and then stirred for 3 hours. The reaction mixture was cooled to room temperature and then poured into 200 ml of ice water. An aqueous solution of sodium hydroxide was added to the resultant mixture to alkalify the latter. The mixture thus obtained was stirred for 1 hour, and the resulting precipitate was collected by filtration. The filter cake was dissolved in 100 ml of benzene. The solution thus formed was washed successively with a dilute aqueous solution of sodium hydroxide and then with water, and was thereafter dried over anhydrous magnesium sulfate. After the removal of the drying agent, the solution was fractionated by chromatography on a silica gel column (eluent: benzene). Relevant eluates were concentrated so that 3.5 g of an aldehyde compound were obtained in the form of a brown oil. The aldehyde compound was left over, whereby it was solidified into a yellow solid (sintered at 93° C. and higher).

EXAMPLE 6

In a ball mill were ground and mixed 0.5 g of a polyester resin ("VYRON 200", trade name: product of Toyobo Co., Ltd.), 0.5 g of the above-exemplified tetrakisazo dye (A-9) and 50 g of tetrahydrofuran. The resulting dispersion was coated onto an aluminum plate by means of a wire bar and then dried at 80° C. for 20 minutes, whereby a charge-generating layer of about 0.5 μm thick was formed.

Over the charge-generating layer, a solution which had been formed by dissolving 1 g of Exemplary Compound No. 1 and 1 g of a polycarbonate resin ("PANLITE K-1300", trade name; product of Teijin Chemicals Ltd.) in 10 g of chloroform was coated by a wire bar. The thus-coated solution was dried at 80° C. for 30 minutes into a charge-transporting layer having a thickness of about 18 μm, whereby the layer-built photoreceptor shown in FIG. 2 was fabricated.

Using an electrostatic copying Paper testing apparatus (Model: "EPA-8100", trade name; manufactured by Kabushk Kaisha Kawaguchi Denki Seisakusyo, the photoreceptor was charged by a corona discharge at an impression voltage of —6 KV. The surface potential $V_0$ at that time was measured. The photoreceptor was left over for 2 seconds in a dark place, and the surface potential $V_2$ at that time was measured. Light was then irradiated from a halogen lamp (color temperature: 2856° K) in such a state that the surface illuminance of the photoreceptor became 5 lux, whereby the time passed by until the surface potential dropped to one half of $V_2$ was measured and the half-value exposure $E_{\frac{1}{2}}$ (lux.sec) was calculated. In addition, the surface potential $V_{12}$ upon an elapsed time of 10 seconds after the irradiation of light, namely, the residual potential was also measured.

EXAMPLES 7-25

In a similar manner to Example 6, various photoreceptors were fabricated by using certain hydrazone compounds of the present invention and the above tetrakisazo compounds as charge-transporting materials and charge-generating materials respectively, and their $E_{\frac{1}{2}}$ were determined. The results are shown together with those of Example 6 in Table 3.

TABLE 3

| | Charge-generating material | Charge-transporting material | $V_0(v)$ | $V_2(v)$ | $V_{12}(v)$ | $E_{\frac{1}{2}}$ (lux.sec) |
|---|---|---|---|---|---|---|
| Ex. 6 | A-9 | No. 1 | −1180 | −1155 | 0 | 0.6 |
| Ex. 7 | A-9 | No. 2 | −975 | −960 | 0 | 0.7 |
| Ex. 8 | A-9 | No. 13 | −1015 | −995 | 0 | 1.4 |
| Ex. 9 | A-1 | No. 1 | −820 | −820 | 0 | 0.8 |
| Ex. 10 | A-15 | No. 1 | −1210 | −1185 | 0 | 1.0 |
| Ex. 11 | A-15 | No. 14 | −1080 | −1060 | 0 | 1.2 |
| Ex. 12 | A-22 | No. 2 | −935 | −920 | 0 | 0.9 |
| Ex. 6 | A-9 | No. 1 | −1180 | −1155 | 0 | 0.6 |
| Ex. 7 | A-9 | No. 2 | −975 | −960 | 0 | 0.7 |
| Ex. 8 | A-9 | No. 13 | −1015 | −995 | 0 | 1.4 |
| Ex. 9 | A-1 | No. 1 | −840 | −820 | 0 | 0.8 |
| Ex. 10 | A-15 | No. 1 | −1210 | −1185 | 0 | 1.0 |
| Ex. 11 | A-15 | No. 14 | −1080 | −1060 | 0 | 1.2 |
| Ex. 12 | A-22 | No. 2 | −935 | −920 | 0 | 0.9 |
| Ex. 13 | A-40 | No. 1 | −940 | −920 | 0 | 0.9 |
| Ex. 14 | A-40 | No. 13 | −1020 | −1000 | 0 | 2.0 |
| Ex. 15 | A-49 | No. 2 | −845 | −830 | 0 | 1.9 |
| Ex. 16 | A-49 | No. 5 | −720 | −700 | −1 | 2.4 |
| Ex. 17 | A-53 | No. 1 | −1110 | −1085 | 0 | 1.5 |
| Ex. 18 | A-53 | No. 14 | −995 | −975 | −1 | 2.0 |
| Ex. 19 | A-59 | No. 2 | −1210 | −1180 | 0 | 1.3 |
| Ex. 20 | A-59 | No. 13 | −1050 | −1035 | 0 | 1.8 |
| Ex. 21 | A-153 | No. 1 | −840 | −820 | 0 | 1.3 |
| Ex. 22 | A-153 | No. 2 | −1127 | −1005 | −1 | 1.4 |
| Ex. 23 | A-153 | No. 3 | −890 | −840 | 0 | 1.3 |
| Ex. 24 | A-153 | No. 5 | −1110 | −1040 | −1 | 1.6 |
| Ex. 25 | A-153 | No. 13 | −946 | −914 | 0 | 1.5 |

EXAMPLES 26–34

In a similar manner to Example 6, various photoreceptors were fabricated by using the phthalocyanine compounds shown in Table 2 and certain hydrazone compounds of the present invention as charge-generating materials and charge-transporting materials respectively, and their $E_{\frac{1}{2}}$ were determined. The results are shown in Table 4, along with the charge-generating materials and charge-transporting materials used.

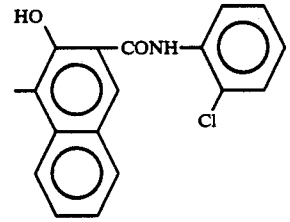

TABLE 4

| | Charge-generating material | Charge-transporting material | $V_0(v)$ | $V_2(v)$ | $V_{12}(v)$ | $E_{\frac{1}{2}}$ (lux.sec) |
|---|---|---|---|---|---|---|
| Ex. 26 | P-1 | No. 1 | −980 | −940 | 0 | 1.5 |
| Ex. 27 | P-2 | No. 2 | −1020 | −975 | −1 | 1.4 |
| Ex. 28 | P-6 | No. 1 | −1100 | −1040 | 0 | 1.0 |
| Ex. 29 | P-6 | No. 6 | −870 | −840 | −1 | 1.6 |
| Ex. 30 | P-6 | No. 13 | −920 | −890 | −2 | 2.0 |
| Ex. 31 | P-7 | No. 1 | −945 | −920 | 0 | 1.2 |
| Ex. 32 | P-7 | No. 16 | −990 | −965 | 0 | 1.7 |
| Ex. 33 | P-10 | No. 1 | −1080 | −980 | 0 | 1.0 |
| Ex. 34 | P-12 | No. 1 | −1080 | −920 | −10 | 1.2 |

EXAMPLES 35–59

Dis-azo compounds (CG-1), (CG-2), (CG-3) and (CG-4) represented by the following structural formulae:

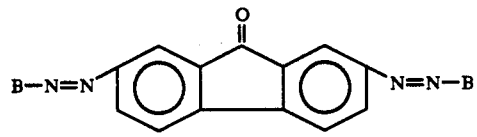
(CG-1)

wherein B represents

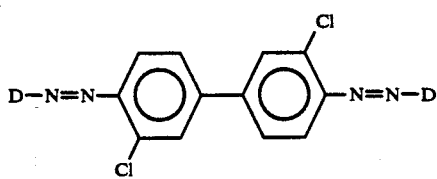
(CG-2)

wherein D represents

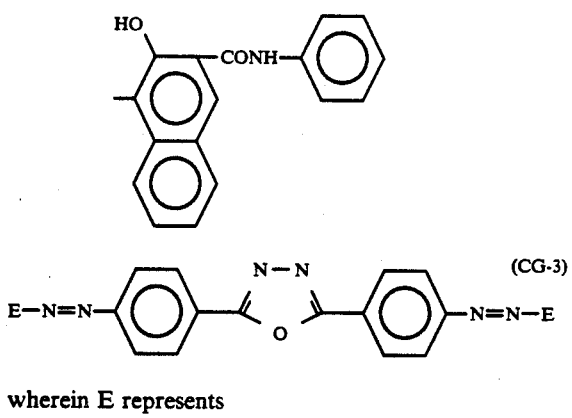

wherein E represents

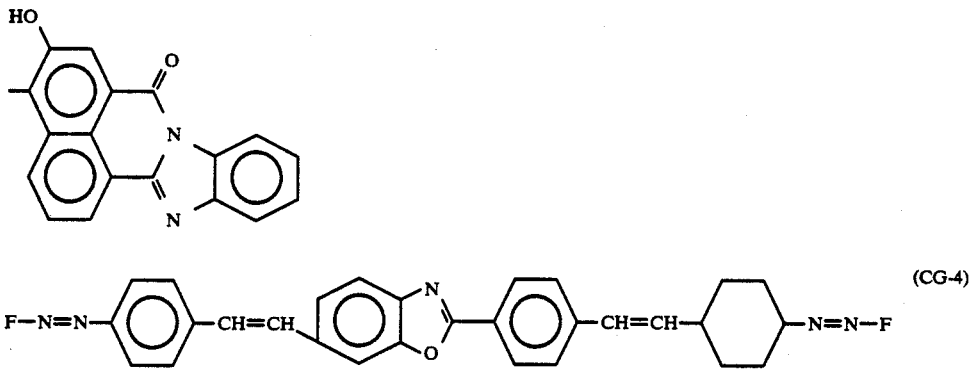

wherein F represents

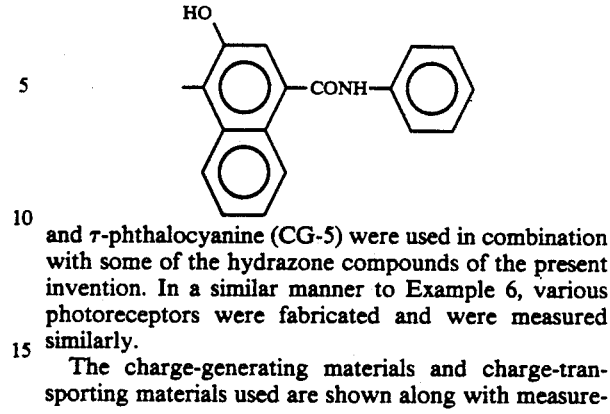

and τ-phthalocyanine (CG-5) were used in combination with some of the hydrazone compounds of the present invention. In a similar manner to Example 6, various photoreceptors were fabricated and were measured similarly.

The charge-generating materials and charge-transporting materials used are shown along with measurement results in Table 5.

TABLE 5

| | Charge-generating material | Charge-transporting material | $V_0(v)$ | $V_2(v)$ | $V_{12}(v)$ | $E_{\frac{1}{2}}$ (lux.sec) |
|---|---|---|---|---|---|---|
| Ex. 35 | CG-1 | No. 1 | −920 | −875 | 0 | 1.0 |
| Ex. 36 | CG-1 | No. 2 | −1040 | −980 | 0 | 1.1 |
| Ex. 37 | CG-1 | No. 3 | −984 | −970 | 0 | 1.0 |
| Ex. 38 | CG-1 | No. 5 | −1210 | −1120 | −1 | 1.4 |
| Ex. 39 | CG-1 | No. 7 | −940 | −890 | 0 | 2.0 |
| Ex. 40 | CG-1 | No. 13 | −1240 | −1200 | −1 | 1.2 |
| Ex. 41 | CG-1 | No. 15 | −970 | −920 | 0 | 1.5 |
| Ex. 42 | CG-2 | No. 1 | −1016 | −998 | 0 | 2.4 |
| Ex. 43 | CG-2 | No. 2 | −1000 | −976 | −2 | 3.0 |
| Ex. 44 | CG-2 | No. 3 | −1120 | −1000 | 0 | 2.0 |
| Ex. 45 | CG-2 | No. 6 | −940 | −800 | −1 | 4.5 |
| Ex. 46 | CG-2 | No. 8 | −920 | −810 | 0 | 2.2 |
| Ex. 47 | CG-3 | No. 1 | −880 | −790 | 0 | 1.8 |
| Ex. 48 | CG-3 | No. 2 | −1060 | −920 | 0 | 2.0 |
| Ex. 49 | CG-3 | No. 3 | −1140 | −1020 | −1 | 3.1 |
| Ex. 50 | CG-3 | No. 4 | −930 | −840 | 0 | 2.0 |
| Ex. 51 | CG-3 | No. 15 | −847 | −770 | −1 | 3.7 |
| Ex. 52 | CG-4 | No. 2 | −1110 | −1050 | 0 | 2.0 |
| Ex. 53 | CG-4 | No. 3 | −1190 | −1000 | −1 | 2.5 |
| Ex. 54 | CG-4 | No. 5 | −1240 | −1150 | 0 | 2.2 |
| Ex. 55 | CG-4 | No. 7 | −980 | −890 | 0 | 2.4 |
| Ex. 56 | CG-5 | No. 1 | −925 | −900 | 0 | 1.9 |
| Ex. 57 | CG-5 | No. 3 | −875 | −800 | −1 | 2.2 |
| Ex. 58 | CG-5 | No. 16 | −1050 | −980 | 0 | 2.0 |
| Ex. 59 | CG-5 | No. 18 | −1010 | −950 | 0 | 2.1 |

COMPARATIVE EXAMPLES 1-5

Compounds (CT-1), (CT-2), (CT-3) and (CT-4) represented by the following structural formulae:

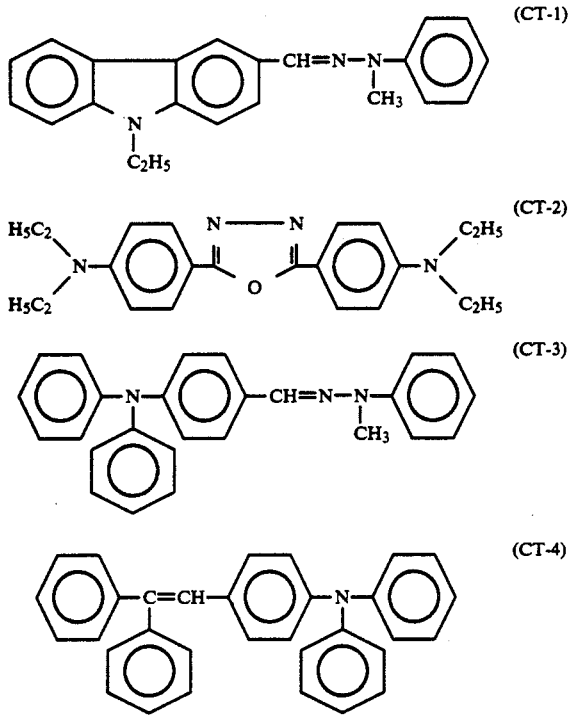

were used as charge-transporting materials instead of the compounds of the present invention, while the above-described dis-azo compounds (CG-1), (CG-2) and (CG-3) were employed as charge-generating materials. In a similar manner to Example 6, various photoreceptors were fabricated and were measured similarly. The charge-generating materials and charge-transporting materials used are shown along with measurement results in Table 6.

TABLE 6

|  | Charge-generating material | Charge-transporting material | $V_0(v)$ | $V_2(v)$ | $V_{12}(v)$ | $E_{\frac{1}{2}}$ (lux.sec) |
| --- | --- | --- | --- | --- | --- | --- |
| Comp. Ex. 1 | CG-1 | CT-2 | −1150 | −970 | −1 | 3.8 |
| Comp. Ex. 2 | CG-2 | CT-1 | −975 | −820 | −4 | 12.0 |
| Comp. Ex. 3 | CG-2 | CT-3 | −1010 | −850 | −1 | 5.7 |
| Comp. Ex. 4 | CG-2 | CT-4 | −830 | −780 | −2 | 4.2 |
| Comp. Ex. 5 | CG-3 | CT-2 | −1210 | −1100 | −1 | 5.6 |

EXAMPLE 60

Using the photoreceptors fabricated in Examples 6, 7, 25 and 31, charging and exposure operations were repeated 1,000 times to measure variations in charging characteristics. The results are shown in Table 7.

TABLE 7

| Photo-receptor | Number of repetitions | $V_0(v)$ | $V_2(v)$ | $V_{12}(v)$ | $E_{\frac{1}{2}}$ (lux.sec) |
| --- | --- | --- | --- | --- | --- |
| Ex. 6 | 1st | −1180 | −1155 | 0 | 0.6 |
|  | 1000th | −1165 | −1140 | 0 | 0.6 |
| Ex. 7 | 1st | −975 | −960 | 0 | 0.7 |
|  | 1000th | −970 | −955 | 0 | 0.8 |
| Ex. 25 | 1st | −946 | −914 | 0 | 1.5 |
|  | 1000th | −940 | −900 | −1 | 1.6 |
| Ex. 31 | 1st | −945 | −920 | 0 | 1.2 |
|  | 1000th | −940 | −915 | 0 | 1.2 |

COMPARATIVE EXAMPLE 6

Using the photoreceptors fabricated in Comparative Examples 1, 2 and 3, charging and exposure operations were repeated 1,000 times to measure variations in charging characteristics. The results are shown in Table 8.

TABLE 8

| Photo-receptor | Number of repetitions | $V_0(v)$ | $V_2(v)$ | $V_{12}(v)$ | $E_{\frac{1}{2}}$ (lux.sec) |
| --- | --- | --- | --- | --- | --- |
| Comp. Ex. 1 | 1st | −1150 | −970 | −1 | 3.8 |
|  | 1000th | −950 | −800 | −5 | 5.4 |
| Comp. Ex. 2 | 1st | −975 | −820 | −4 | 12.0 |
|  | 1000th | −800 | −670 | −10 | 18.0 |
| Comp. Ex. 3 | 1st | −1010 | −850 | −1 | 5.7 |
|  | 1000th | −905 | −760 | −8 | 9.2 |

EXAMPLE 61

Using the photoreceptors fabricated in Examples 31 and 33, their sensitivities to lights in the semiconductor laser range were measured. Used as a measuring instrument was a similar electrostatic copying paper testing apparatus to Example 6. However, monochromatic lights obtained by spectroscopically separating halogen light at 780 nm and 830 nm, respectively were used as irradiation sources. The monochromatic lights were each irradiated to give the light intensity of 10 $\mu W/cm^2$ on the surface of each photoreceptor. The results are shown in Table 9, in which each sensitivity is shown by the inverse number of $E_{\frac{1}{2}}$ (unit: $cm^2/\mu J$).

TABLE 9

| Photo-receptor | Wavelength of Light | $V_0(v)$ | $V_2(v)$ | $V_{12}(v)$ | $E_{\frac{1}{2}}^{-1}$ (lux.sec) |
| --- | --- | --- | --- | --- | --- |
| Ex. 31 | 780 nm | −930 | −890 | 0 | 1.0 |
|  | 830 nm | −925 | −895 | −1 | 1.0 |
| Ex. 33 | 780 nm | −890 | −850 | 0 | 1.2 |
|  | 830 nm | −890 | −850 | −10 | 1.0 |

As has been described above, electrophotographic photoreceptors using a hydrazone compound of the present invention having high sensitivity and can exhibit stable performance even when used repeatedly. Further, they also have excellent durability.

The photoreceptors according to the present invention can be widely not only in electrophotographic copy machines but also in various printers and electrophotographic plate-making systems which make use of the principle of electrophotographic copying.

As demonstrated, for example, in Example 61, photoreceptors fabricated using a hydrazone compound of this invention and a phthalocyanine compound represented by the formula (V) are effective for printers which use a semiconductor laser beam as a light source.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an electrophotographic photoreceptor comprising a photosensitive layer formed on an electrically conductive base and containing a charge-generating material and a charge-transporting material, the improvement wherein the charge-transporting material is a hydrazone compound represented by the following formula (I):

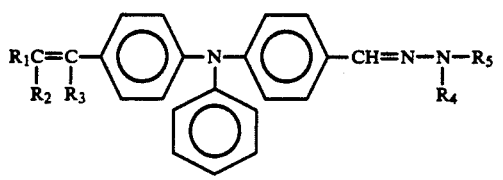

(I)

wherein $R_1$ and $R_2$ individually represent an aryl group or collectively with the carbon atom to which they are attached a polycyclic group, $R_3$ represents a halogen atom, an alkyl or phenyl group, and $R_4$ and $R_5$ each represent an alkyl, aralkyl or aryl group, with the proviso that at least one of $R_4$ and $R_5$ is an aryl group.

2. The photoreceptor of claim 1, wherein in Formula I, $R_4$ is phenyl.

3. The photoreceptor of claim 1, wherein in Formula I, $R_3$ is a chlorine atom.

4. The photoreceptor of claim 1, wherein in Formula I, $R_1$ and $R_2$ are each phenyl.

5. The photoreceptor of claim 1, wherein in Formula I, $R_5$ is phenyl.

6. The photoreceptor of claim 1, wherein in Formula I, $R_5$ is methyl.

7. The photoreceptor of claim 1, wherein in Formula I, $R_1$ and $R_2$ and $R_4$ is phenyl.

8. The photoreceptor of claim 1, wherein in Formula I, $R_1$ and $R_2$ collectively with the carbon atom to which they are attached are 9-fluorenglidene, 10-xanthenylidene or 10-thioxanthenylidene.

9. The photoreceptor of claim 1, wherein the charge-generating material is an azo compound represented by the following formula (IV):

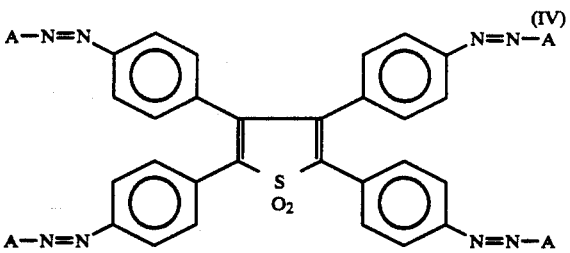

wherein each A represents a coupler residuum.

10. The photoreceptor of claim 1, wherein the charge-generating material is a compound represented by the following formula (V):

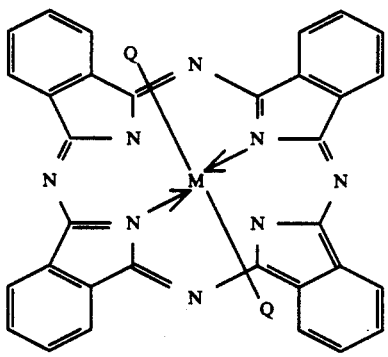

wherein M represents Si, Ge or Sn and Q represents a hydroxyl group or a chlorine, bromine, iodine or fluorine atom.

11. The photoreceptor of claim 1, wherein the photosensitive layer is a monolayer in which the charge-generating material and the charge-transporting material are dispersed in a binder.

12. The photoreceptor of claim 1, wherein the photosensitive layer comprises a charge generation layer with the charge-generating material dispersed in a binder and a charge transportation layer with the charge-transporting material dispersed in a binder.

* * * * *